United States Patent
Kleinsorgen et al.

[11] Patent Number: 6,165,499
[45] Date of Patent: Dec. 26, 2000

[54] TRANSDERMAL THERAPEUTIC SYSTEM WITH SMALL APPLICATION-AREA THICKNESS AND GREAT FLEXIBILITY, AND PRODUCTION PROCESS

[75] Inventors: Reinhard v. Kleinsorgen; Britta v. Kleinsorgen, both of Bendorf, Germany

[73] Assignee: LTS Lohmann Therapie-Systeme GmbH, Germany

[21] Appl. No.: 09/155,334

[22] PCT Filed: Mar. 12, 1997

[86] PCT No.: PCT/EP97/01252

§ 371 Date: Apr. 26, 1999

§ 102(e) Date: Apr. 26, 1999

[87] PCT Pub. No.: WO97/35564

PCT Pub. Date: Oct. 2, 1997

[30] Foreign Application Priority Data

Mar. 25, 1996 [DE] Germany ............................ 196 11 684
Mar. 4, 1997 [DE] Germany ............................ 197 08 674

[51] Int. Cl.[7] ....................................................... A61K 9/14
[52] U.S. Cl. ............................ 424/449; 424/448; 602/41; 602/60; 602/61; 604/890.1; 604/19; 604/289; 604/290; 604/304; 604/307
[58] Field of Search ..................................... 424/449, 448; 602/41, 60, 61; 604/890.1, 19, 289, 290, 304, 307

[56] References Cited

U.S. PATENT DOCUMENTS 4,624,665 11/1986 Nuwayser ................................ 604/307
4,915,950 4/1990 Miranda et al. ......................... 424/448
5,064,422 11/1991 Wick ....................................... 604/307
5,780,047 7/1998 Kamiya et al. ......................... 424/443
5,843,472 12/1998 Ma et al. ................................ 424/449

FOREIGN PATENT DOCUMENTS 0285563 3/1988 European Pat. Off. .
0400078 2/1989 European Pat. Off. ........ A61F 13/02
2006969 2/1970 Germany .
2908432 3/1979 Germany .
3939376 11/1989 Germany .

*Primary Examiner*—S. Mark Clardy
*Assistant Examiner*—Michael A. Williamson
*Attorney, Agent, or Firm*—James Klaniecki; Ann W. Speckman

[57] ABSTRACT

A transdermal therapeutic system for the release of active substances to a substrate is characterized by the structure of the system comprising a substrate (1) provided with a separating layer (2), a film layer (3) comprising the active substance, and a protective layer (4) provided with a non-stick finish, the separating layer (2) consisting of a material whose bond to the film layer (3) may be abolished. By means of printing methods, such systems having small application thickness and high flexibility can be manufactured, it being possible to provide a substrate that has been rendered adhesive as an alternative to the substrate/separating layer-complex. A printing method limiting the active substance-containing region to the application site reduces disposal problems.

24 Claims, 2 Drawing Sheets

TRANSDERMAL THERAPEUTIC SYSTEM WITH SMALL APPLICATION-AREA THICKNESS AND GREAT FLEXIBILITY, AND PRODUCTION PROCESS

This application is a 371 of PCT/EP97/01252 filed Mar. 12, 1997.

BACKGROUND OF THE INVENTION

The present invention relates to a transdermal therapeutic system for the controlled release of active substances to human or animal skin, which stands out for its small application thickness and high flexibility, as well as to processes suitable for its production.

TECHNICAL FIELD OF THE INVENTION

Systems for the controlled release of active substances to human or animal skin are known, among others, as so-called Transdermal Therapeutic Systems (TTS) or "Transdermal Delivery Systems" (TDS). Depending on their construction and type of active substance release one differentiates between so-called bag or reservoir systems and matrix systems. In the former case, these systems consist of a flat bag which comprises an active substance. One side thereof is impermeable to active and inactive ingredients and the opposite side is semipermeable and formed as a control membrane which is coated with an adhesive for adhesion to the skin. Owing to its complicated construction, production of the system requires a great deal of expenditure, since the individual components are to be produced separately and must then be joined to form a system. Moreover, the thickness of the system impairs the wearing properties. In addition, bag-type systems involve the risk of so-called "drug dumping", that is, the sudden substantial active substance release to the skin, for example, as a result of physical destruction of the membrane or bag. EP 0 285 563 describes such a transdermal therapeutic system for the combined application of estrogens and gestagens. U.S. Pat. No. 4,624,665 describes systems comprising the active substance in microencapsulated form within the reservoir. The reservoir is embedded between backing layer and membrane. The edge of the system is provided with a pressure-sensitive adhesive. Construction and production of this system are very complicated since the active substance must be microencapsulated and homogeneously distributed and then be embedded between backing layer and membrane. In addition, the system must be provided with an adhesive edge and covered with a protective layer. Matrix systems usually consist of a backing layer which is impermeable to active substances and auxiliaries and averted from the skin and an adhesive layer wherein active substance is distributed. For the purpose of protecting the adhesive layer it is provided with an antiadhesively finished protective film which has to be removed prior to application. DE-OS 20 06 969 describes such a system wherein contraceptive substances are incorporated in the adhesive component or adhesive film. This publication discloses that the adhesive film may be an acrylate. Similar to labels, matrix systems have the disadvantage that they are punched out from a self-adhesive laminate positioned on a nonstick protective layer. The stampings on the protective layer are separated in a further step to produce the finished TTS. The regions between the individual punched pieces, which consist of active substance-containing adhesive layer and backing layer, are to be disposed of as active substance-containing waste. DE 39 39 376, DE 29 08 432 and EP 0 400 078 B1 represent examples providing solutions for avoiding such waste.

The thickness of the system which results from the production method and the kind of application is a disadvantage of known matrix systems. This thickness affects the system's flexibility and therefore its wearing properties, whereas wearing comfort of the system increases with decreasing thickness. Moreover, known matrix systems are limited by the fact that neither at the same time nor in chronological order it is possible to provide alternative doses, active substance concentrations, or varying chemical system compositions differing in the active substance or a special active substance combination and providing a desired application of several active substances, which differs with respect to time or site.

SUMMARY OF THE INVENTION

It is the object of the present invention to provide a transdermal therapeutic matrix system that avoids the above-mentioned disadvantages and difficulties, has a very good flexibility including improved wearing properties owing to a reduced thickness, and which permits the production of so-called "multi-dose" units consisting of several separable "single-dose" systems. These may differ with respect to the parameters type of active substance/concentration of active substance/system area/system thickness/chemical composition of the system, and they are therefore capable of providing alternative doses at the same time or in chronological order by means of a "multi-dose" unit.

In a device for releasing an active substance to a substrate this object is achieved with the present invention by the form according to the characterizing features of claim 1.

For this reason, the present invention meets the demands of the object by providing a system having improved wearing properties resulting from good flexibility owing to its small thickness. Moreover, the production technology of the system according to the present invention makes it possible to produce so-called "multi-dose" units consisting of separable "single-dose" systems. These "single-dose" systems of a "multi-dose" unit may be the same or different, the parameters causing the differences may be:

kind of active substance, active substance concentration per system, area of a system, thickness of a system, and chemical composition of the system.

A "multi-dose" release unit therefore enables alternative doses to be offered at the same time or in chronological order. "Multi-dose" units according to the present invention may also be "single-dose" systems differing in the active substance itself or in active substance combinations, making it possible to provide a specific desired application of several active substances at different times.

Therefore, the system according to the present invention offers a lower-priced alternative to known systems.

Most surprisingly it turned out that the principle of so-called "decalcomanias"="decals" or "tattoos" is particularly suitable as active substance carriers or application systems in transdermal therapy. The term "tattoo", formerly used in connection with "artistic" skin pigmentation, has been adopted in literature for the use of "decalcomanias" for decoration purposes.

"Decals" are "transfer pictures" for decoration purposes known in ceramic industry, for example. They consist of a paper substrate which is provided with a solvent-soluble separating layer and has lacquer layers thereon. The paper is moistened with solvent either prior to or during joining the lacquer layer with the stoneware, whereupon the separating layer dissolves. The lacquer layer may now be pushed from the paper carrier to find its place on the substrate to be decorated. The composite may be strengthened by baking.

DETAILED DESCRIPTION OF THE INVENTION

Figure 1:
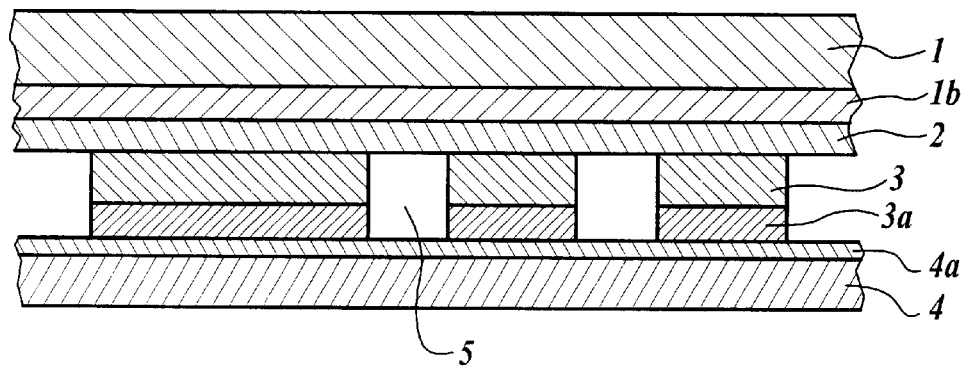
FIG. 1 illustrates a sectional view of a "multi-dose" unit with three "single-dose" systems.

A decal for the transdermal use of active substances advantageously has the following structure:

A soluble separating layer is applied on a substrate consisting either of a paper, fabric, nonwoven, or a polymeric layer permeable to solvents, e.g., a polymeric membrane. Differentiation of this laminate into two individual layers may be supported by a barrier layer which prevents components from reaching the substrate during application. A capillary active insoluble substrate provided with a soluble separating layer is essential. The thickness of the substrate is in the range of 20–200 $\mu$m, preferably 50–120 $\mu$m, and according to a preferred form 60–90 $\mu$m. The separating layer has a thickness of 5–50 $\mu$m, preferably 20–40 $\mu$m. The separating layer connected with the substrate is provided with an active substance-containing film layer. This may be a laminate whose individual layers may be different. For example, the laminate layer facing the separating layer may be free of active substances. To achieve better contact to the skin, the laminate layer averted from the separating layer may be adhesive. The individual layers of the laminate may be the same or different with respect to their polymer base.

In a "multi-dose" unit the substrate provided with the separating layer is printed with several flat-shaped island-like regions of the active substance-containing film layer. Suitable printing methods include any printing method or spraying process or nozzle application method known to the skilled artisan which permit application of an active substance-containing film layer at the required weight uniformity. The active substance-containing film layer may be applied in one or several individual printing steps; similar to a multicolor print, only partial regions of the first print may be printed. In the embodiment according to the present invention is turned out to be advantageous to apply the film layer by means of screen printing. Thus it is possible to apply several differently sized, island-like, active substance-containing film layer regions on one carrier section, which, like in a "multicolor print", differ in their composition, layer thickness, and active substance (different pigment).

Owing to the very small thickness and optimum flexibility the system according to the present invention—in contrast to conventional systems—is suitable for permanent application even on difficult sites of the body, e.g., the region of the ear, the genital region, or on toe-nails and fingernails. Owing to the possibilities of decoration it is also possible to wear the systems on body surfaces which are not covered by clothes.

In a special embodiment, wherein the film layer has no additional pressure-sensitive adhesive layer, a film layer region opposite the separating layer has self-tackiness at the time of application. This is achieved by the fact that the layer region is also moistened when the separation layer dissolves, and the swollen regions of the polymeric film layer obtain adhesive properties which enable a bond to be formed to the skin, but which are lost on the skin-averted side of the film layer after volatilization of the solvent. The thickness of the film layer is in the range of 5–50 $\mu$m, preferably 5–30 $\mu$m, and in a special embodiment 10–25 $\mu$m. The whole surface of the above-mentioned film layer or of the individual regions of the film layer or of the film layer islands is covered with a protective layer which may have an antiadhesive finish. In case of an island-like embodiment of the film layer regions on a common substrate in the "multi-dose" system, the protective layer and the substrate may be perforated in the region between the "islands", so that partial regions can be removed as a "single dose" by tearing them off from the total system. The thickness of the protective layer ranges from 50–100 $\mu$m. For the purpose of application, the protective layer of the system is removed and film layer with substrate applied on the application site in such a manner that the substrate is averted from the application site, whereupon it is moistened with a solvent. In a preferred embodiment water is used as solvent. Owing to the capillary properties of the carrier, the water reaches the separating layer which has been rendered water-soluble for this case; in its solubilized or dissolved state it loses the bond to the film layer, so that the substrate may be peeled off the film layer, with the film layer remaining on the site of application.

In case the separating layer is water-soluble, it has the chemical nature, for example, of a saccharide or polysaccharide, polyhydroxy alcohol, polyvinyl pyrrolidone or another water-soluble polymer, such as polyethylene glycol or gelatin. In case the separating layer is fat-soluble, it is of the chemical nature of a triglyceride or a wax. According to a special embodiment for this case, the separating layer may be provided such that it liquefies under the influence of heat and thereby loses the bond to the film layer. The film layer may consist of film-forming polymers. Suitable film-forming polymers include: hydroxypropyl cellulose, hydroxypropyl methylcellulose, polyvinyl pyrrolidone, vinylpyrrolidone-vinyl acetate copolymer 40:60, ethylcellulose, acrylic-acid ester copolymers and methacrylic acid ester copolymers with trimethylammonium methyl acrylate, copolymers of dimethylaminomethacrylic acid and neutral methacrylic acid esters, shellac, cellulose acetate phthalate, hydroxypropyl methylcellulose phthalate, polymers of methacrylic acid and methacrylic acid esters, ethyl acrylate-methacrylic acid methyl ester copolymer 70:30, methacrylic acid-methyl acrylate copolymer 50:50, gelatin, polyvinyl acetate, methacrylate, acrylate dispersions, polyether-polyamide block copolymer, polyethylene-methyl-methacrylate block copolymer, polyurethanes, polyester block copolymer, polyisobutylene-styrene-styrene copolymers, styrene-butadiene-styrene-isoprene copolymers, ethylene-vinyl acetate copolymers, polyamide, nitrocellulose, as well as further lacquer or film formers known to the skilled artisan. Inevitably softeners are added to these film formers in accordance with the required necessary flexibility of the film. In the form of a laminate that layer of this film layer which faces the application site may be pressure-sensitive adhesive by means of components stated below. Components in this sense include any conventional adhesive known to the skilled artisan and also used for wound toilet in the form of dressings and patches, for example, adhesives based on acrylates, polyisobutylene, polyurethanes, silicones, etc. The protective layer which consists of a paper or polymer coated with a silicone resin is known to the skilled artisan in different designs. It is obtainable from the specialized trade as adhesive protective layer or "release liner" provided with a siliconization adapted to the adhesive. The perforation which may be punched into the system represents a separate variant of the system. Thereby it is possible to obtain a unit with several equal or different dosages and periods of action. This is particularly useful when one or several drugs or combinations are to be administered over a certain period in a certain dose strength. The substrate may be printed with the same or different drugs and/or drug combinations in the form of spaced apart areas by means of screen printing. This is desirable in cyclic hormone therapy with estradiol or gestagens, for example.

In the context of the present invention the term "active substances" is to be understood as chemical elements, organic and inorganic compounds which are capable of migrating from the components of the generic device containing them and thus cause an intended effect. Human and veterinary medicine, as well as the use with plants, represent particularly important fields of application for the device according to the present invention.

The active substances to be released preferably serve the dermal treatment of local skin diseases, the intradermal and transdermal treatment of diseases, the treatment of wounds, or the skin care in cosmetic preparations. In a special embodiment, the film layer serves as a carrier of high-volatile active substances which are released outwardly, i.e., in the direction of the side averted from the skin. These also include flavoring substances such as perfume oils having an active substance character in a wider sense (olfactory substances).

Local anaesthetics, local antibiotics, antiseptics, antimycotics, antihistaminics, and antipruritic drugs; keratolytics and caustic drugs; virustatics, antiscabietic agents, steroids, as well as different substances for the treatment of acne, psoriasis, photodermatoses, or precancerous stages are used for the dermal treatment of local skin diseases. Active substances applicable by the intradermal route include, for example, steroid and non-steroid antirheumatics, local anaesthetics, substances stimulating the blood flow, or vaso-protectors and vasoconstrictors to treat vascular diseases, as well as active substances to influence processes in the subcutaneous fatty tissue. Transdermally applicable active substances include, for example, analgesics, anti-arrhythmic drugs, narcotics and their antagonists, neuroleptics, hormones or hormone substitutes, antidepressants, tranquilizers, hypnotics, psychostimulants, antiparkinson drugs, ganglionic blockers, sympathomimetics, alpha-sympatholytics, beta-sympatholytics, antisympathotonics, anti-asthmatics, antiemetics, appetite depressants, diuretics, or active substances for weight reduction, etc. Because of the small thickness of the system according to the present invention preferred active substances are those developing their action already at very low concentrations. Examples of these preferred active substances include steroids, such as estradiol, estriol, progesterone, norethisterone, norethindrone, levonorgestrel and their derivatives, as well as estradiol diacetate, norgestamate, gestagens, desogestrel, demegestrone, promegestrone, testosterone, hydrocortisones and their derivatives; nitro compounds, such as amyl nitrate, nitroglycerin, isosorbide dinitrate; amine compounds, such as nicotine, chlorpheniramine, terfenadine, and triprolidine; oxicam derivatives such as piroxicam; mucopolysaccharases such as thiomucase; opioid substances such as buprenorphine, morphine, fentanyl and their salts, derivatives or analogues, naloxone, codeine, dihydroergotamine, lysergic acid derivatives, pizotiline, salbutamol, terbutaline; prostaglandins, such as PGA, PGB, PGE and the PGF-series, for example, misoprostol and enprostil, omeprazol, imipramine; benzamides, such as metoclopramines and scopolamine; peptides and growth factors such as EGF, TGF, PDGF, etc; somatostatin; clonidin; dihydropyridines, such as nifedipine, nitrendipine, verapamil, diltiazem, ephedrine, propanolol, metoprolol, spironolactone; thiazides such as hydrochlorothiazide and flunarizine. Styptic active substances and wound-cleansing substances, such as enzymes, antiseptics, disinfectants, and antibiotics; pain-relieving agents and anaesthetic active substances, as well as active substances promoting wound healing to stimulate granulation, to induce vascularization, or to promote epithelization are used for the treatment of wounds.

In a preferred embodiment for transdermal use, the film layer comprises a steroid hormone, preferably estradiol either alone or combined with other drugs, which is used in transdermal application for hormone substitution during postmenopause or for the treatment of osteoporosis. On the other hand, the device for the release of estradiol may also be applied on long-term wounds, for instance crural ulcera, for the treatment of wounds. In another preferred embodiment of the device according to the present invention, the film layer comprises vegetable preparations, such as extracts or tinctures. These may be used for the treatment of topical skin diseases, for example, oak bark extract, walnut extract, tincture of arnica, hamamelis extract, ribwort extract, pansy extract, thyme or sage extract; for the treatment of damaged or injured skin, for example, St. John's wort tincture, cone flowers tincture, chamomile flowers extract, or calendula flowers tincture; and for the care of exhausted and damaged skin, for example, birch leaves extract, nettle extract, coldsfoot extract, comfrey tincture, horsetail extract, or aloe vera extract. Vegetable preparations may also be released from the film layer for the intradermal treatment of diseases, for example, extracts of horse chestnut and butcher's broom in case of vein diseases, or extracts and tinctures of arnica, calendula, and capsicum in case of contusions, distortions, or haemorrhages. Vegetable preparations in the system according to the present invention may also be used in transdermal therapy, for example, ginseng extract in case of geriatric complaints; valerian tincture, extracts of melissa and hop to cause a sedative effect in case of superexcitation, sleep disturbances, and stress; extracts of kola and tea to achieve a stimulative effect; or hawthorn extract to stabilize the circulatory system.

In particular cases where the active substance or active substance extract itself has film-forming properties, the film layer merely consists of the active substance or the corresponding extract. According to a preferred embodiment the film layer of the system according to the present invention consists of tobacco powder extract. Such a device can be used by smokers as an alternative to tobacco, cigarettes or similar tobacco products. This system is also suitable for the use with film-forming vegetable and animal extracts, the number of which is not listed here exhaustively. Another special embodiment relates to the use of the system according to the present invention as carrier of narcotics, psychopharmaceuticals, and agents for treating Alzheimer's disease and senile dementia. These highly potent drugs require a system ensuring wearing properties for several days and a waste-free production. These requirements are met by screen printing the active substance-containing film layer and by the flexibility and layer thickness of the system.

According to the present invention the individual film layer segments can also be marked in the form of colors, letters, numbers, dates, codes, pictographs and the like by means of screen printing. Inevitably, there is the possibility of dyeing the film layer by means of soluble dyes or pigments. Moreover, the system may also be completely transparent.

Figure 2:
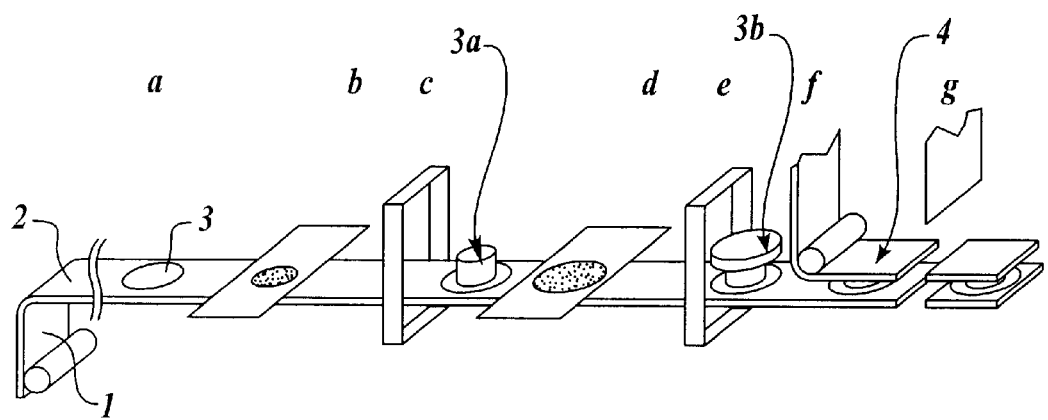
FIG. 2 shows a schematic production device.

The system according to the present invention may be manufactured as mentioned hereunder:

A paper of 150 g (100–200 g/m$^2$), which has been produced from an aluminum sulfate-free pulp stock comprising in addition to starch kaolin as filler, is superficially spread with a sizing solution and dried. Coating is effected such that only the pores of the outermost paper layer are covered. On the paper carrier such treated a solution of polyvinyl alcohol is applied by means of a coating bar or gravure roll, followed by drying. The paper so obtained, which is provided with the separating layer (polyvinyl alcohol) and is present in the form of rolls for further use, serves as substrate for the following printing process carried out according to the screen printing method. Depending on the design of the system, differing numbers of printing steps and stencils are necessary. The example shown in FIG. 2 is not intended to limit the present invention. First, the system name is printed on the substrate by means of screen printing using a commercial color. After that, the first layer of the active substance-containing film layer, which is on the outside after application, is printed. In the example shown, printing is carried out using an active substance-free polyacrylate dispersion (Polyacrylate Dispersion 30 percent Ph.Eu.) with 10% acetyltriisobutyl citrate which forms a film of 5 µm after drying. The screen printing stencil is dimensioned such that the area of the final system is defined by means of this printing procedure. Then, the active substance-containing layer is printed. This is carried out directly on the complete surface of the polyacrylate layer. Examples of the composition of this printing medium are listed in the following (parts by weight):

| a) | estriol | 4 |
|---|---|---|
|  | N,N-diethyl-m-toluamide | 4 |
|  | acetone | 50 |
|  | Eudragit E 30 D | 40 |
|  | Plastoid E 35 | 10 |
| b) | buprenorphine | 10 |
|  | isopropyl lanolate | 10 |
|  | Plastoid E 35 | 65 |
| c) | estradiol | 4 |
|  | Polyacrylate Dispersion 30 percent (Ph.Eu) | 100 |
|  | triethyl citrate | 4 |
|  | propylene glycol | 4 |
|  | acetone | 10 |
|  | polyvinyl pyrrolidone | 4 |
|  | lecithin | 1 |
|  | ethanol | 20 |

In Example c), a 5 µm-layer with Plastoid E 35 is additionally printed. (Plastoid and Eudragit are trade names of Rhöbm GmbH).

After printing, the last layer is provided with the protective layer.

In the following details, features, and advantages of the present invention are illustrated in greater detail with reference to the drawings.

In the Figures the numbers have the following meanings:

| FIG. 1: | 1 | substrate |
|---|---|---|
|  | 1b | barrier layer |
|  | 2 | separating layer |
|  | 3 | film layer |
|  | 3a | adhesive layer |
|  | 4a | nonstick layer |
|  | 4 | protective layer |
|  | 5 | perforation |
| FIG. 2: | 1 | substrate |
|  | 2 | separating layer |
|  | 3 | nonstick layer of the film layer laminate averted from the substrate |
|  | 3a | active substance-containing layer of the film layer laminate |
|  | 3b | adhesive layer of the film layer laminate |
|  | 4 | protective layer |

Onto film layer (3), which has been manufactured by means of a printing process, film layer (3a) is applied in (a) on substrate (1) by means of screen printing (b) and is dried in (c). In (d) film layer (3b) is applied, again by screen printing, which is dried in (e). In (f) the protective layer (4) is laminated. In (g) cutting to form the finished system is carried out.

Figure 3:
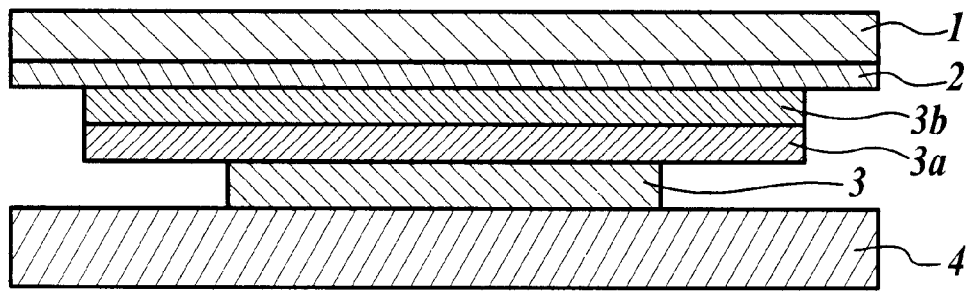
FIG. 3 presents a sectional view of a transdermal system according to the present invention.
Figure 4:
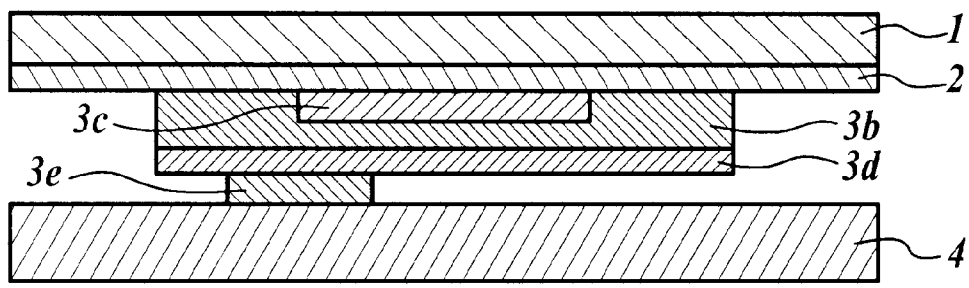
FIG. 4 shows a sectional view of another transdermal combination system.

| FIG. 3: | 1 | substrate |
|---|---|---|
|  | 2 | separating layer |
|  | 3a | adhesive layer free from active substance |
|  | 3b | film layer free from active substance |
|  | 3 | active substance-containing film layer |
|  | 4 | protective layer |
|  | 3a + 3b + 3 = | film layer laminate |
| FIG. 4 | 1 | substrate |
|  | 2 | separating layer |
|  | 3c | pictorial representation |
|  | 3d | active substance-containing film layer active substance 1 |
|  | 3e | active substance-containing film layer active substance 2 |
|  | 4 | protective layer |
|  | 3c + 3d + 3e = | film layer laminate |

As a matter of course, the production of active substance layers, in particular such layers having narrow outlines—which is particularly useful with respect to process engineering and for obtaining thin-layer and flexible systems—is not restricted to transdermal therapeutic systems that are produced starting from a substrate provided with a separating layer that is dissolved or liquefied upon application so that the substrate can be removed.

Rather, it is possible to obtain flat-shaped or sheet-like systems for the release of active substances to the skin by employing one or several printing processes. The size of the system with respect to its area can be determined by the first printing process; as an alternative, the size of the systems can also be determined by one of the subsequent printing processes. The printing process determining the size of the system can be carried out, partially or on the entire surface, onto a substrate that is provided with a non-stick finish. It is of use if at least the backing layer of the finished TTS and/or the self-adhesive matrix layer which comes into contact with the skin is/are formed by the printing medium, which in the latter case may comprise one or several active substances. If the backing layer of the TTS is formed as a print layer it can be used as information carrier for printing with marks or designations, and/or be printed in color. The backing layer which is formed as a printing layer may be provided with a supporting film or sheet provided with an abhesive finish, the abhesiveness of which is smaller than that of the printed substrate. This means that the invention comprises systems for the controlled release of active substances to the human or animal skin, on the basis of systems which are based exclusively on one or several printing methods.

Most surprisingly, it turned out that the processes of printing, for example, T-shirts with images or letters, in particular for obtaining a sufficiently flexible layer thickness, are also suitable for the production of transdermal therapeutic systems if a substrate that has been rendered abhesive is printed instead of fabrics or nonwovens. The printing methods being employed for the production of rub-off letters, such as Letraset®, for example, can be transformed to the production of complete TTS, too. The thickness of the substrate—similar to that of the substrate provided with a separating layer—is in the range of 20–200 $\mu$m, preferably 50–120 $\mu$m, and 60–90 $\mu$m in a particularly preferred form, and it is rendered abhesive by a siliconized layer, for example. To achieve an improved bond to the skin, the layer of printing media adjacent to and in contact with the substrate may be rendered adhesive. The active substance-containing film layer may be applied in one or several individual printing steps, it being also possible to print partial areas of the previous print, similar to a multi-color print. Suitable printing methods are again all those known to the skilled artisan which enable uniform application of an active substance-containing film layer while maintaining the required weight uniformity. Die individual layers of the individual printing layers to be printed may be the same or differ in respect of their polymer base body. It has proved to be of advantage to apply the film layer by screen-printing. In this way it is possible to obtain several island-like active substance-containing film layer regions of different size on a substrate, which regions differ in their composition, layer thickness and active substance (different pigment)—as is similary the case in a "multi-color print". The thickness of the film layer is in the range of 5–50 $\mu$m, preferably 5–30 $\mu$m, and in a special embodiment in the range of 10–25 $\mu$m, and the layer is of rubber-like consistency.

For the purpose of application, the substrate of the system is removed, and the remaining system is applied to the application site. Suitable printing media include the film-forming polymers and masses mentioned hereinabove.

This film layer may be in the form of a laminate and be rendered pressure-sensitive adhesive by the components mentioned hereinbelow which are contained in the layer facing the application site. Suitable components in this connection are any commercial adhesives known to those skilled in the art that are also used in wound treatment in the form of dressings and patches, such as, for example, adhesives based on acrylates, polyisobutylenes, silicones, etc.

The term "active substance" again has the same meaning as mentioned hereinabove. All mentioned active substances and special features of application again apply in the same manner as to the system formed with a substrate and separating layer.

The system may be manufactured in an analogous manner as follows:

A paper of 150 g (100–200 g/m$^2$), siliconized, serves as a substrate for the printing process, which is effected using the screen-printing method. Depending on the design of the system, a different number of printing steps and printing stencils are required. As a rule, it is the printing medium that is employed first which comprises the active substance, this printing medium being rendered pressure-sensitive adhesive. The printing medium which is used thereafter at last forms the size of the system. It is, for example, rubber-like and film-forming. The complete print image that has been applied to the substrate may be covered by a polypropylene film which later-on serves as a supporting film and which is rendered abhesive.

What is claimed is:

1. A transdermal therapeutic system for application of an active substance-releasing layer of small thickness to a treatment site, characterized by a capillary active insoluble substrate having a thickness of 20–200 $\mu$m bonded to a soluble separating layer having a thickness of 5–50 $\mu$m, a film layer having a thickness of 5–50 $\mu$m bonded to the soluble separating layer and which contains the active substance, and a protective layer having a thickness of 50–100 $\mu$m provided with a nonstick finish contacting and covering the film layer on the side opposite to which the separating layer is bonded, wherein the separating layer comprises a material whose bond to the film layer may be abolished through solubilization, dissolution or liquefaction, following application of the layered system to the treatment site.

2. The transdermal therapeutic system according to claim 1 characterized in that the soluble separating layer comprises a water-soluble film-forming substance.

3. The transdermal therapeutic system according to claim 1 characterized in that the soluble separating layer comprises a fat-soluble film-forming substance.

4. The transdermal therapeutic system according to claim 1 characterized in that the soluble separating layer comprises a film-forming substance that is both water-soluble and fat-soluble.

5. The transdermal therapeutic system according to claim 1 characterized in that the soluble separating layer is a substance that can be liquified by a temperature elevation to above 40° C.

6. The transdermal therapeutic system according to one of claims 2–5 characterized in that the soluble separating layer has a layer thickness of 20–40 $\mu$m.

7. The transdermal therapeutic system according to claim 1 characterized in that the substrate consists of a porous material.

8. The transdermal therapeutic system according to claim 1 or 7 characterized in that the substrate has a layer thickness of 50–120 $\mu$m.

9. The transdermal therapeutic system according to claim 1 characterized in that the active substance-containing film layer represents a laminate.

10. The transdermal therapeutic system according to claim 9 characterized in that the individual layers are different with respect to at least one of the parameters area, layer thickness, and composition and that at least one layer comprises at least one active substance.

11. The transdermal therapeutic system according to claim 10 characterized in that the active substances in the film layer are introduced in regions separated from each other.

12. The transdermal therapeutic system according to claim 1 characterized in that the active substance-containing film layer is self-adhesive on the side of the protective layer.

13. The transdermal therapeutic system according to claim 1 characterized in that the film layer comprises one or several film-forming polymers.

14. The transdermal therapeutic system according to claim 1 characterized in that the film layer has a layer thickness of 5–30 µm.

15. The transdermal therapeutic system according to claim 1 characterized in that the film layer is distributed in spaced apart sections on the substrate.

16. The transdermal therapeutic system according to claim 1, characterized in that the film layer is formed by one or several printing process steps on the substrate, which is provided with the soluble separating layer.

17. A process for the production of a transdermal therapeutic system according to claim 1, characterized by one or more printing process steps using one or more printing media for producing the active substance-containing film layer between the substrate, which substrate has been provided with the soluble separating layer, and the covering protective layer, wherein the transdermal therapeutic system has a defined size.

18. The process according to claim 17 characterized in that the first printing procedure determines the defined size of the transdermal therapeutic system with respect to its area.

19. The process according to claim 17 characterized in that the size of the system is determined by one of the subsequent printing procedures.

20. The process according to claim 17 characterized in that the printing process which determines the size of the system is effected partially or completely onto a substrate which has been rendered abhesive or which has been provided with a soluble or liquefiable separating layer.

21. The process according to claim 17 characterized in that the printing media is suitable for the formation of an application surface of the film layer.

22. The process according to claim 17 characterized in that the printing media is suitable for the formation of a self-adhesive matrix layer which comes into contact with the skin.

23. The process according to claim 17 characterized in that the printing media contains one or more active substances.

24. The process according to claim 17 characterized in that the print layer which serves to form the application surface is printed for the purpose of making or designating or coloring.

* * * * *